United States Patent
Silverman et al.

(10) Patent No.: US 10,098,347 B2
(45) Date of Patent: Oct. 16, 2018

(54) METHODS OF IMPROVING GROWTH AND STRESS TOLERANCE IN PLANTS

(71) Applicant: Valent BioSciences LLC, Libertyville, IL (US)

(72) Inventors: Franklin Paul Silverman, Highland Park, IL (US); Marci Ann Surpin, Highland Park, IL (US); Derek D. Woolard, Zion, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 1 day.

(21) Appl. No.: 15/585,433

(22) Filed: May 3, 2017

(65) Prior Publication Data

US 2017/0318807 A1   Nov. 9, 2017

Related U.S. Application Data

(60) Provisional application No. 62/330,999, filed on May 3, 2016.

(51) Int. Cl.
   *A01N 37/44*   (2006.01)
   *A01N 37/42*   (2006.01)

(52) U.S. Cl.
   CPC ............ *A01N 37/44* (2013.01); *A01N 37/42* (2013.01)

(58) Field of Classification Search
   CPC .................................. A01N 37/44; A01N 37/42
   See application file for complete search history.

(56) References Cited

U.S. PATENT DOCUMENTS

2008/0318783 A1*  12/2008  Wilson, Jr. ............ A01N 37/42
                                                    504/136

OTHER PUBLICATIONS

Yang, Z. et al., Differential Effects of Abscisic Acid and Glycine Betaine on Physiological Responses to Drought and Salinity Stress for Two Perennial Grass Species, 2012, J. Amer. Soc. Hort. Sci., vol. 137, Issue 2, pp. 96-106.*

Mira, H. et al., The interaction effect of drought and exogenous application of glycine betaine on corn (*Zea mays* L.), 2013, European Journal of Experimental Biology, vol. 3, Issue 5, pp. 197-206.*

Hassanein, R. et al., Improving Salt Tolerance of *Zea Mays* L. Plans by Presoaking Their Grains in Glycine Betaine, 2009, Australian Journal of Basic and Applied Sciences, vol. 3, Issue 2, pp. 928-942.*

* cited by examiner

*Primary Examiner* — John Pak
*Assistant Examiner* — Andriae M Holt
(74) *Attorney, Agent, or Firm* — Wood, Phillips, Katz, Clark & Mortimer

(57) ABSTRACT

The present invention is directed to methods of improving plant growth by applying an effective amount of (S)-abscisic acid and glycine betaine to the plant. The present invention is further directed to methods of improving stress tolerance in a plant by applying an effective amount of (S)-abscisic acid and glycine betaine to the plant.

20 Claims, No Drawings

METHODS OF IMPROVING GROWTH AND STRESS TOLERANCE IN PLANTS

FIELD OF THE INVENTION

The present invention is generally directed to methods of improving plant growth and stress tolerance comprising applying effective amounts of (S)-abscisic acid and glycine betaine to a plant.

BACKGROUND OF THE INVENTION

Growers continually attempt to grow the most productive crops possible in order to maximize yields. Plant growth regulators are one tool that growers can use in order to influence the growth of their plants based on the restrictions of water and temperature. The effects of plant growth regulators on plants under different conditions can vary widely. Further, predicting the effect that application of more than one plant growth regulator simultaneously applied to the plant is difficult.

(S)-abscisic acid ("(S)-ABA") is an endogenous corn plant growth regulator with many roles in growth and development. For example, (S)-ABA inhibits seed germination, thus antagonizing gibberellins, which stimulate the germination of grains. (S)-ABA promotes stress tolerance and maintains growth under stress conditions (see Sharp R E et al., Root growth maintenance during water deficits: physiology to functional genomics, *J Exp Bot*, 2004 November, 55(407), 2343-2351). Interestingly, several studies have shown that maintaining 'normal' ABA levels in well-watered plants is required to maintain shoot growth in tomato (Sharp R E et al., Endogenous ABA maintains shoot growth in tomato independently of effects on plant water balance: evidence for an interaction with ethylene, *J Exp Bot*, 2000 September, 51(350), 1575-1584) and Arabidopsis (LeNoble M E et al., Maintenance of shoot growth by endogenous ABA: genetic assessment of the involvement of ethylene suppression, *J Exp Bot*, 2004 January, 55(395), 237-245). Moreover, (S)-ABA is responsible for the development and maintenance of dormancy in seeds and woody plants, which when deficient in ABA often demonstrate pre-harvest sprouting of seeds due to a lack of dormancy induction.

Further, applications of (S)-ABA have also been shown to provide protection from chilling and drought, as well as to increase the red color of seedless table grapes. Examples of effective commercially available (S)-ABA formulations include ProTone™ and Contego™ (available from Valent BioSciences LLC).

Glycine betaine ("GB") is a solute that accumulates in plants, micro-organisms and fungi in response to abiotic stress. Among the major cereal crops, only rice does not naturally accumulate GB (Shirasawa K. et al., Accumulation of glycine betaine in rice plants that overexpress choline monooxygenase from spinach and evaluation of their tolerance to abiotic stress, *Ann Bot*, 2006 September, 98(3), 565-571). Overexpression of bacterial or plant genes in rice to produce GB resulted in low accumulation of GB, but conferred stress tolerance. Exogenous application of GB to plants has been shown to confer abiotic stress tolerance (Chen and Murata, Glycine betaine: an effective protectant against abiotic stress in plants, *Trends Plant Sci*, 2008 September, 13(9), 499-505). This includes stress resistance inducing resistance to chilling, freezing, and drought across multiple plant species. However, the levels of stress protection observed, although significant, do not reach commercially acceptable thresholds.

Accordingly, there is a need in the art for new methods to improve the growth of plants under abiotic stress conditions.

SUMMARY OF THE INVENTION

In one aspect, the present invention is directed to methods of improving plant growth comprising applying an effective amount of (S)-abscisic acid ((S)-ABA) and glycine betaine (GB) to the plant, wherein the weight ratio of (S)-ABA:GB is from about 1:1 to about 1:33.

In another aspect, the present invention is directed to method of improving stress tolerance in a plant comprising applying an effective amount of (S)-ABA and GB to the plant, wherein the weight ratio of (S)-ABA:GB is from about 1:1 to about 1:33.

DETAILED DESCRIPTION OF THE INVENTION

Applicant unexpectedly discovered that a mixture of (S)-abscisic acid ("(S)-ABA") and glycine betaine ("GB") improved stress tolerance and plant growth under stress conditions.

In one embodiment, the present invention is directed to methods of improving plant growth comprising applying an effective amount of (S)-ABA and GB to the plant.

In another preferred embodiment, the plant in which plant growth is improved is subject to an abiotic stress.

In another embodiment, the present invention is directed to methods of improving stress tolerance in a plant comprising applying an effective amount of (S)-ABA and GB to the plant.

In a preferred embodiment, the stress tolerance that is improved is to an abiotic stress.

In another preferred embodiment, (S)-ABA and GB are applied at a weight ratio from about 1:1 to about 1:33.

In one embodiment, the plant is a monocotyledonous plant or a dicotyledonous plant. In a preferred embodiment, the monocotyledonous plant is a grass, more preferably corn. In another preferred embodiment, the dicotyledonous plant is an herbaceous or woody dicot, more preferably cucumber or basil.

In another embodiment, the plant is genetically modified. In a preferred embodiment, the genetically modified plant expresses herbicide resistance, insect resistance, drought tolerance or increased physiological function.

In another embodiment, the plant is subjected to cold stress. As used herein, cold stress refers to conditions of lower temperature (e.g. 4-10° C.) wherein plant growth is significantly slowed as compared to greenhouse conditions that support optimal growth and development.

In another embodiment, the plant is subjected to drought stress. As used herein, drought stress refers to watering conditions wherein plant growth is significantly slowed as compared to those where water availability is sufficient to support optimal growth and development.

In a preferred embodiment, (S)-ABA and GB are applied prior to the advent of abiotic stress. As used herein, this can refer to a number of different types of stress including cold and or drought. In the case of cold stress, the (S)-ABA and GB composition is applied prior to cold temperature, as a protection against chilling damage. When the intended stress is drought, application of (S)-ABA and GB prior to drought stress allows for banking of soil water. By inhibiting water use during vegetative-phase growth, there is more water present to support reproductive-phase growth, when yield losses due to water stress are higher.

In a preferred embodiment (S)-ABA and GB are applied during the vegetative growth stage period beginning at V2 and ending at VT. Applicant has referred to corn developmental stages throughout the application as "V" stages. The "V" stages are designated numerically as V1, V2, V3, etc. In this identification system of V(n), (n) represents the number of leaves with visible collars. Each leaf stage is defined according to the uppermost leaf whose leaf collar is visible (see Corn Growth and Development, 2011. Abendroth, L, Elmore, R, Boyer, M and Marlay, S, Iowa State University Press). "VT" refers to tassel emergence growth stage and is not an early vegetative stage of corn.

In another embodiment, from about 1 to about 100 grams of (S)-ABA per hectare are applied to corn. In a preferred embodiment, from about 2 to about 75 grams of (S)-ABA per hectare are applied to corn.

In another embodiment, from about 1 to about 100 grams of (S)-ABA per hectare are applied to cucumber. In a preferred embodiment, from about 2 to about 75 grams of (S)-ABA per hectare are applied to cucumber.

In another embodiment, from about 1 to 100 grams of (S)-ABA per hectare are applied to basil. In a preferred embodiment, from about 2 to about 75 grams of (S)-ABA per hectare are applied to basil.

In yet another embodiment, from about 1 to about 1,000 grams of GB per hectare are applied to the plant. In a more preferred embodiment, from about 2 to about 800 grams of GB per hectare is applied to the plant.

In another embodiment, application of GB increases the (S)-ABA activity providing improved stress tolerance and improved plant growth.

In another embodiment, the (S)-ABA and GB can be applied with an herbicide such as glyphosate, mesotrione, halosulfuron, saflufenacil or dicamba.

In another embodiment, the (S)-ABA and GB can be applied with a fungicide such as tetraconazole, metconazole, a strobilurin, or a combined strobilurin-azole product.

In another embodiment, the (S)-ABA and GB can be applied with an insecticide such as methylparathion, bifenthryn, esfenvalerate, lorsban, carbaryl or lannate.

In yet another embodiment, the (S)-ABA and GB can be applied with foliar fertilizers such as CoRoN (available from Helena Chemical), a controlled-release nitrogen, or Bio-Forge (available from Stoller USA), which is largely N,N'-diformyl urea, or other micro nutrient-containing sprays.

The (S)-ABA and GB mixture can be applied by any convenient means. Those skilled in the art are familiar with the modes of application that include foliar applications such as spraying, dusting, and granular applications; soil applications including spraying, in-furrow treatments, or side-dressing.

In another preferred embodiment, the present invention is directed to a composition comprising (S)-ABA and GB, wherein the weight ratio of (S)-ABA:GB is from about 1:1 to about 1:33.

Aqueous spray solutions utilized in the present invention generally contain from about 0.01% to about 0.5% (v/v) of a non-ionic surface-active agent.

The surface active agent comprises at least one non-ionic surfactant. In general, the non-ionic surfactant may be any known non-ionic surfactant in the art. Suitable non-ionic surfactants are in general oligomers and polymers. Suitable polymers include alkyleneoxide random and block copolymers such as ethylene oxide-propylene oxide block copolymers (EO/PO block copolymers), including both EO-PO-EO and PO-EO-PO block copolymers; ethylene oxide-butylene oxide random and block copolymers, C2-6 alkyl adducts of ethylene oxide-propylene oxide random and block copolymers, C2-6 alkyl adducts of ethylene oxide-butylene oxide random and block copolymers, polyoxyethylene-polyoxypropylene monoalkylethers, such as methyl ether, ethyl ether, propyl ether, butyl ether or mixtures thereof; vinylacetate/vinylpyrrolidone copolymers; alkylated vinylpyrrolidone copolymers; polyvinylpyrrolidone; and polyalkyleneglycol, including the polypropylene glycols and polyethylene glycols. Other non-ionic agents are the lecithins; and silicone surface active agents (water soluble or dispersible surface active agents having a skeleton which comprises a siloxane chain e.g. Silwet L77®). A suitable mixture in mineral oil is ATPLUS® 411.

As used herein, "effective amount" refers to the amount of the (S)-ABA and/or GB that will improve growth, drought stress tolerance, cold stress tolerance, and/or yield. The "effective amount" will vary depending on the (S)-ABA and GB concentrations, the plant species or variety being treated, the severity of the stress, the result desired, and the life stage of the plants, among other factors. Thus, it is not always possible to specify an exact "effective amount." However, an appropriate "effective amount" in any individual case may be determined by one of ordinary skill in the art.

As used herein, "improving" means that the plant has more of the quality than the plant would have had it if it had not been treated by methods of the present invention.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1

To determine the capacity of glycine betaine ("GB") to confer thermo-tolerance, both singly and in combination with (S)-abscisic acid ("(S)-ABA"), chilling (i.e. cold) tolerance assays were performed using Italian large leaf basil (*Ocimum basilicum*) seedlings. Basil seeds were sterilized in an ethanol solution containing 0.16% Maxim® XL fungicide (Maxim is a registered trademark of and available from Syngenta Corporation). The sterilized seeds were germinated on ½×Murashige and Skoog Basal Salt Media, supplemented with 1× Gamborg's Vitamins and 0.6% Phytagar, and dispensed into 24-well plates. Plates with sown seeds were sealed with surgical tape and placed in a growth chamber running diurnal cycles of 12 hours of light at 24° C. and 12 hours of darkness at 19° C. The seedlings were allowed to germinate and grow for five days.

After five days, concentrated solutions of GB and/or (S)-ABA were added as an overlay in 0.4% Phytagar. The plates were re-sealed and placed back into the growth chamber for 48 hours. After 48 hours, the plates were transferred to a chamber with identical light settings, but with the temperature set at 6° C. during the day and 2° C. at night. The seedlings were subjected to chilling stress for six days, after which time they were transferred back to the ambient temperature chamber, and scored after a six-day recovery period.

Individual wells contained indicated amounts of GB and/or (S)-ABA. Stock solutions of (S)-ABA were prepared in dimethyl sulfoxide ("DMSO"), and the final concentration of DMSO in all wells was 0.5%. Positive control wells contained a final concentration of 20 ppm (S)-ABA (~20 mg/l) and 0.5% DMSO; negative control wells contained 0.5% DMSO. GB was evaluated singly at concentrations of 0, 3,000, 10,000, 30,000, and 100,000 milligrams per liter ("mg/l".) To test whether there was a synergistic interaction between GB and (S)-ABA, glycine betaine was added to the media at concentrations of 0, 1,000, 3,000, 10,000, and 30,000 mg/l, whereas (S)-ABA was held at a concentration of 3 mg/l. After six days of chilling stress and six days of recovery, the seedlings were scored on the amount of necrotic and damaged tissue, the primary indication of chilling stress in basil seedlings. The results are summarized in Table 1 below.

TABLE 1

GB and (S)-ABA Protection against Chilling Injury in Basil Seedlings

| Formulation | GB (mg/l) | 0 mg/l (S)-ABA | 3 mg/l (S)-ABA |
|---|---|---|---|
| 1 | 0 | — | + |
| 2 | 1,000 | NT | + |
| 3 | 3,000 | — | ++ |
| 4 | 10,000 | + | ++ |
| 5 | 30,000 | ++ | ++ |
| 6 | 100,000 | + | NT |

"NT" denotes no data recorded
"—" denotes extensive chilling injury
"+" denotes moderate chilling injury
"++" denotes little to no chilling injury; equivalent to 20 ppm (S)-ABA alone As demonstrated, 30,000 mg/l GB is capable of providing equivalent protection as ~20 mg/l (S)-ABA to Basil seedlings. However, when GB and (S)-ABA are combined only about 1/10 the amount of GB and 1/6 the amount of (S)-ABA are required to provide the equivalent protection to either alone. Although analysis of the data suggests that there may be a greater than an additive effect of the combination of GB and (S)-ABA, further studies were performed to test for interactions within these compositions.

Example 2

A laboratory study was conducted at Long Grove, Ill. Cucumber (*Cucumis sativa* var. Straight Eight) seeds were sown in Pro-Mix® BX potting soil (Pro-Mix is a registered trademark of and available from Premier Horticulture Ltd.) and plants were grown in a CONVIRON® growth chamber at 25° C. under a 16:8 (light:dark) photoperiod. At 15 days post-sowing, plants were subjected to sprays with a portable Preval® paint sprayer. All spray solutions were made up in deionized water and a non-ionic surfactant was added to all spray solutions at 0.05% (v/v). At 48 hours post-spraying, plants were moved to a CONVIRON® growth chamber and subjected to a temperature of 4° C. for 48 hours under a 12:12 (light:dark) photoperiod. Upon removal from the cold chamber, plants were returned to a CONVIRON® growth chamber set at 25° C. under a 16:8 (light:dark) photoperiod. The plants were visually scored for chilling damage at 72 hours post-chilling. Each treatment was replicated seven times. Results are summarized in Table 2 below.

TABLE 2

72 hours Post-Chilling Damage in Cucumber following Spray Treatment with (S)-ABA, GB, or the Combination

| Treatment | Ratio GB:ABA | % Leaf Area Damaged | Synergy Factor |
|---|---|---|---|
| Control | 0 | 76.4 | n/a |
| (S)-ABA 300 mg/l | 0:1 | 52.9 | n/a |
| GB 300 mg/l | 1:0 | 84.3 | n/a |
| GB 1,000 mg/l | 1:0 | 82.1 | n/a |
| GB 3,000 mg/l | 1:0 | 46.4 | n/a |
| GB 300 mg/l + (S)-ABA 300 mg/l | 1:1 | 10.7 | 3.74 |
| GB 1,000 mg/l + (S)-ABA 300 mg/l | 3.3:1 | 25.0 | 2.68 |
| GB 3,000 mg/l + (S)-ABA 300 mg/l | 10:1 | 18.6 | 1.24 |

As demonstrated in Table 2, the mixtures of the present invention at a ratio of 1:1 to 10:1 GB:(S)-ABA showed more than an additive effect at preventing cold stress damage. Using the following formula, Applicant was able to determine that the response to the GB:(S)-ABA ratio was synergistic, in which a synergy factor is calculated by the Abbott method:

$$\% \ C_{exp} = A + B - (AB/100),$$

where % $C_{exp}$ is the expected efficacy and "in which A and B are the increase in growth (or resistance to stress) levels given by the single [plant growth regulators]. If the ratio between the experimentally observed efficacy of the mixture $C_{obs}$ and the expected efficacy of the mixture is greater than 1, synergistic interactions are present in the mixture" (Gisi, Synergistic Interaction of Fungicides in Mixtures, The American Phytopathological Society, 86:11, 1273-1279, 1996). To be conservative Applicant has set the minimum synergy factor to 1.1 throughout the Examples. Applicant determined synergy to be present at the following ratios of GB:(S)-ABA: 1:1 (synergy factor 3.74); 3.3:1 (synergy factor 2.68) and 10:1 (synergy factor 1.24).

Example 3

A laboratory study was conducted at Long Grove, Ill. Italian sweet basil seeds were sown in Pro-Mix® BX potting soil and plants were grown at room temperature under cool-white fluorescent lights under a 16:8 (light:dark) photoperiod. At 22 days post-sowing, plants were subjected to sprays with a portable Preval® paint sprayer. At 48 hours post-spraying, plants were moved to a CONVIRON® growth chamber and subjected to a temperature of 4° C. for 72 hours under a 12:12 (light:dark) photoperiod. Upon removal from the cold chamber, plants were returned to the laboratory and placed again under the cool white fluorescent lamps until they were visually scored for chilling damage at 24 hours and 72 hours post-chilling. Each treatment was replicated seven times. Results are summarized in Table 3 below.

TABLE 3

Chilling Damage of Italian Sweet Basil following Spray Treatment with (S)-ABA, GB, or the Combination

| | | % Leaf Area Damaged | | Synergy Factor | |
|---|---|---|---|---|---|
| | Ratio | 24 h post- | 72 h post- | | |
| Treatment | GB:ABA | chilling | chilling | 24 h | 72 h |
| Control | 0 | 63 | 73 | n/a | n/a |
| (S)-ABA 300 mg/l | 0:1 | 12 | 27 | n/a | n/a |
| (S)-ABA 1,000 mg/l | 0:1 | 6 | 14 | n/a | n/a |
| GB 3,000 mg/l | 1:0 | 67 | 79 | n/a | n/a |
| GB 20,000 mg/l | 1:0 | 45 | 65 | n/a | n/a |
| GB 3,000 mg/l + (S)-ABA 300 mg/l | 10:1 | 5 | 14 | 1.15 | 1.26 |
| GB 20,000 mg/l + (S)-ABA 300 mg/l | 66.7:1 | 39 | 60 | 0.44 | 0.32 |

As demonstrated in Table 3, the mixtures of the present invention at a 10:1 ratio of GB:(S)-ABA showed more than an additive effect at preventing cold stress damage, while the 66.7:1 ratio did not confer even additive protection. Using the Abbot method described in Example 2 above, Applicant determined that the response to the 10:1 GB:(S)-ABA ratio was synergistic (synergy factor 1.15 at 24 hours and 1.26 at 72 hours), but not at the 66.7:1 ratio of GB:(S)-ABA (synergy factor 0.44 at 24 hours and 0.32 at 72 hours).

Example 4

A laboratory study was conducted at Long Grove, Ill. Italian sweet basil seeds were sown in Pro-Mix® BX potting soil and plants were grown at room temperature under cool-white fluorescent lights under a 16:8 (light:dark) photoperiod. At 22 days post-sowing, plants were subjected to sprays with a portable Preval® paint sprayer. At 48 hours post-spraying, plants were moved to a CONVIRON® growth chamber and subjected to a temperature of 4° C. for 72 hours under a 12:12 (light:dark) photoperiod. Upon removal from the cold chamber, plants were returned to the laboratory and placed again under the cool-white fluorescent lamps until they were visually scored for chilling damage at 24 hours and 120 hours post-chilling. Each treatment was replicated seven times. Results are summarized in Table 4 below.

TABLE 4

Chilling Damage of Italian Sweet Basil Following Spray Treatment with (S)-ABA, GB, or the Combination

| | | % Leaf Area Damaged | | Synergy Factor | |
|---|---|---|---|---|---|
| | Ratio | 24 h post- | 120 h post- | | |
| Treatment | GB:ABA | chilling | chilling | 24 h | 120 h |
| Control | 0 | 46.67 | 65.00 | N/A | N/A |
| (S)-ABA 300 mg/l | 0:1 | 23.00 | 41.00 | N/A | N/A |
| (S)-ABA 1,000 mg/l | 0:1 | 11.67 | 21.67 | N/A | N/A |
| GB 10,000 mg/l | 1:0 | 39.17 | 56.67 | N/A | N/A |
| GB 30,000 mg/l | 1:0 | 40.00 | 50.00 | N/A | N/A |
| GB 10,000 mg/l + (S)-ABA 300 mg/l | 33:1 | 10.00 | 20.00 | 1.34 | 1.54 |
| GB 30,000 mg/l + (S)-ABA 300 mg/l | 100:1 | 31.67 | 47.50 | 0.56 | 0.52 |

As demonstrated in Table 4, the mixtures of the present invention at a 33:1 ratio of GB:(S)-ABA showed more than an additive effect at preventing chilling stress damage, while the 100:1 ratio did not confer even additive protection. Using the Abbot method described in Example 2 above, Applicant determined that the response to the 33:1 GB:(S)-ABA ratio was synergistic (synergy factor of 1.34 at 24 hours and 1.54 at 120 hours), but not at the 100:1 ratio of GB:(S)-ABA (synergy factor of 0.56 at 24 hours and 0.52 at 120 hours).

Example 5

A greenhouse study was conducted at Long Grove, Ill. Seeds of a commercial hybrid variety were sown in Pro-Mix® BX in three-liter pots. Greenhouses were kept at 25±3° C. under a 16:8 hour (light:dark) photoperiod, with illumination at canopy level of ~250 µmoles m-2 s-1. Corn was typically fertigated with Peters 21-5-20+ micronutrients, calcium ammonium nitrate and magnesium sulfate. Typical growth rates for corn under these conditions ranged from 4 to 5 centimeters per day.

In this study, spray applications were made to corn at stage V4. These applications were made in a track sprayer outfitted with a 4001E Teejet® nozzle (Teejet is available from and a registered trademark of Spraying Systems Co., Glendale Heights, Ill., USA) and applied at 40 pounds per square inch and at 30 gallons/acre of spray solution. Following spray applications, plants were returned to the greenhouse.

At 3 and 4-days post spray application, stomatal conductance of the 4$^{th}$ true leaf was measured using a Licor Model 6400 XT photosynthesis meter (Licor, Lincoln, Neb.) used according to the manufacturer's directions. For ease of analysis, stomatal conductance values are expressed as a percent of control in Table 5 below.

TABLE 5

Stomatal Conductance of Corn Following Spray

| | Ratio | % of Control Conductance | | Synergy Factor | |
|---|---|---|---|---|---|
| Treatment | GB:ABA | | | | |
| Days Post-Spray | n/a | 3 days | 4 days | 3 days | 4 days |
| Control | n/a | 100 | 100 | n/a | n/a |
| ABA 100 mg/l | 0:1 | 81.3 | 91.8 | n/a | n/a |
| ABA 300 mg/l | 0:1 | 73.6 | 88.7 | n/a | n/a |
| ABA 1,000 mg/l | 0:1 | 76.5 | 95.9 | n/a | n/a |
| ABA 3,000 mg/l | 0:1 | 55.3 | 77.5 | n/a | n/a |
| GB 1,000 mg/l | 0:1 | 86.2 | 97.9 | n/a | n/a |
| GB 1,000 mg/l + ABA 100 mg/l | 10:1 | 60.2 | 84.3 | 1.33 | 1.54 |
| GB 1,000 mg/l + ABA 300 mg/l | 3.3:1 | 53.1 | 71.5 | 1.28 | 2.17 |
| GB 1,000 mg/l + ABA 1,000 mg/l | 1:1 | 52.7 | 64.8 | 1.39 | 5.72 |
| GB 1,000 mg/l + ABA 3,000 mg/l | 0.33:1 | 47.3 | 74.5 | 1.01 | 1.05 |

As demonstrated in Table 5, the mixtures of the present invention at ratios of 10:1, 3.3:1 and 1:1 GB:(S)-ABA showed more than an additive effect at decreasing stomatal conductance, while the 0.33:1 ratio did not confer even an additive decrease. Using the Abbot method described in Example 2 above, Applicant determined synergy to be present at the following ratios of GB:(S)-ABA: 10:1 (synergy factor of 1.33 at 3 days post spraying ("DPS") and 1.54 at 4 DPS); 3.3:1 (synergy factor of 1.28 at 3 DPS and 2.17 at 4 DPS); and 1:1 (synergy factor of 1.39 at 3 DPS and 5.72 at 4 DPS), but not at the 0.33:1 ratio (synergy factor of 1.01 at 3 DPS and 1.05 at 4 DPS). Thus, a ratio of at least 1:1

GB:(S)-ABA is required for the mixture to show synergistic decreases in stomatal conductance.

The invention claimed is:

1. A method of improving plant growth comprising applying an effective amount of (S)-abscisic acid ((S)-ABA) and glycine betaine (GB) to the plant, wherein the weight ratio of (S)-ABA:GB is from about 1:1 to about 1:33.

2. The method of claim 1, wherein the plant is subject to an abiotic stress.

3. The method of claim 2, wherein the abiotic stress is cold stress.

4. The method of claim 2, wherein the abiotic stress occurs prior to the application of (S)-ABA and GB.

5. The method of claim 2, wherein the abiotic stress occurs after the application of (S)-ABA and GB.

6. The method of claim 1, wherein the plant is a monocotyledonous plant.

7. The method of claim 6, wherein the monocotyledonous plant is corn.

8. The method of claim 1, wherein the plant is a dicotyledonous plant.

9. The method of claim 8, wherein the dicotyledonous plant is selected from the group consisting of cucumber and basil.

10. The method of claim 1, wherein (S)-ABA is applied at a rate of about 1 to about 100 grams per hectare and GB is applied at a rate of about 1 to about 1,000 grams per hectare.

11. A method of improving stress tolerance in a plant comprising applying an effective amount of (S)-abscisic acid ((S)-ABA) and glycine betaine (GB) to the plant, wherein the weight ratio of (S)-ABA:GB is from about 1:1 to about 1:33.

12. The method of claim 11, wherein the stress is an abiotic stress.

13. The method of claim 12, wherein the abiotic stress is cold stress.

14. The method of claim 11, wherein the stress occurs prior to the application of (S)-ABA and GB.

15. The method of claim 11, wherein the stress occurs after the application of (S)-ABA and GB.

16. The method of claim 11, wherein the plant is a monocotyledonous plant.

17. The method of claim 16, wherein the monocotyledonous plant is corn.

18. The method of claim 11, wherein the plant is a dicotyledonous plant.

19. The method of claim 18, wherein the dicotyledonous plant is selected from the group consisting of cucumber and basil.

20. A composition comprising (S)-abscisic acid ((S)-ABA) and glycine betaine (GB), wherein the weight ratio of (S)-ABA:GB is from about 1:1 to about 1:33.

* * * * *